United States Patent [19]

Buysch et al.

[11] 4,381,404
[45] Apr. 26, 1983

[54] PROCESS FOR THE PRODUCTION OF N,O-DISUBSTITUTED URETHANES AND USE THEREOF AS STARTING MATERIALS FOR THE PRODUCTION OF ORGANIC ISOCYANATES

[75] Inventors: Hans-Josef Buysch; Heinrich Krimm; Wolfgang Richter, all of Krefeld, Fed. Rep. of Germany

[73] Assignee: Bayer Aktiengesellschaft, Leverkusen, Fed. Rep. of Germany

[21] Appl. No.: 306,070

[22] Filed: Sep. 28, 1981

[30] Foreign Application Priority Data

Oct. 1, 1980 [DE] Fed. Rep. of Germany ....... 3036966

[51] Int. Cl.$^3$ ................ C07C 125/065; C07C 125/073

[52] U.S. Cl. ...................................... 560/24; 560/25; 560/32; 560/115; 560/157; 560/158; 560/162; 560/166

[58] Field of Search .................. 560/24, 25, 157, 115, 560/32, 158, 162, 166

[56] References Cited

U.S. PATENT DOCUMENTS 3,627,813 12/1971 Abbate ................................. 560/24
3,763,217 10/1973 Brill ...................................... 560/24
4,100,351 7/1978 Ramano et al. ...................... 560/24

Primary Examiner—Michael L. Shippen
Attorney, Agent, or Firm—Gene Harsh; Joseph C. Gil; Richard A. Elder

[57] ABSTRACT

The present invention is directed to a process for the production of N,O-disubstituted urethanes comprising reacting N-mono- or N,N'-disubstituted ureas or linear polyureas with aliphatic carbonic esters.

6 Claims, No Drawings

PROCESS FOR THE PRODUCTION OF N,O-DISUBSTITUTED URETHANES AND USE THEREOF AS STARTING MATERIALS FOR THE PRODUCTION OF ORGANIC ISOCYANATES

BACKGROUND OF THE INVENTION

The present invention relates to a new process for the production of N,O-disubstituted urethanes by reaction of N-monosubstituted or N,N'-disubstituted ureas or polyureas with dialkyl carbonates.

The production of lower molecular weight mono- or bis-urethanes, which may be split by the action of heat in a known manner into the isocyanate component thereof and the alcohol component thereof, is gaining in practical interest as a phosgene-free path to the corresponding isocyanates.

It has now surprisingly been found that it is possible to produce simple mono- or bis-urethanes which may be split by the action of heat into isocyanate and alcohol by reaction of N-substituted and, in particular, N,N'-disubstituted ureas with aliphatic carbonic esters. The reaction permits the production of the urethanes in particularly high yields when the catalysts described in detail below are also used.

The reaction according to the present invention is of particular practical interest because:

(a) the reaction between N,N'-disubstituted ureas and aliphatic carbonic esters takes place according to the following equation (wherein R and R' represent the inert radicals of the reactants):

R—NH—CO—NH—R + R'—O—CO—O—R' → 2R—NH—CO—OR' without the formation of by-products; and (b) the substituted ureas or aliphatic carbonic esters to be used as starting materials are obtainable from inexpensive commercially available starting materials.

DESCRIPTION OF THE INVENTION

The present invention relates to a process for the production of N,O-disubstituted urethanes, characterized in that N-mono- or N,N'-disubstituted ureas or linear polyureas are reacted with aliphatic carbonic esters.

The substituted ureas to be used in the process according to the present invention are organic N-mono- or N,N'-disubstituted ureas or linear polyureas, optionally containing urethane or primary terminal amino groups. The ureas useful herein generally have a maximum molecular weight of 5,000, and preferably 2,000. The urea, urethane or amino groups are linked together by means of hydrocarbon radicals. The urea groups may be substituted by hydrocarbon radicals. Any optionally present terminal urethane groups may be substituted at the oxygen atom by hydrocarbon radicals. Typical examples of suitable ureas or polyureas include: N-methylurea, N-ethylurea, N-(n-propyl) urea-, N-(isopropyl)-urea, N-(n-butyl)-urea, N-(iso-butyl)-urea, N-cyclohexylurea, N-benzylurea, N,N'-dimethylurea, N,N'-diethylurea, N,N'-di-(n-butyl)-urea, N,N'-dicyclohexylurea, N,N'-dibenzylurea, N,N'-di-(m-tolyl)-urea, N-phenylurea, N,N'-diphenylurea, N,N'-di-carbamoyl-tolylene diamine-2,4, N,N'-di-carbamoyl-isophorone diamine, or compounds corresponding to the following formulae:

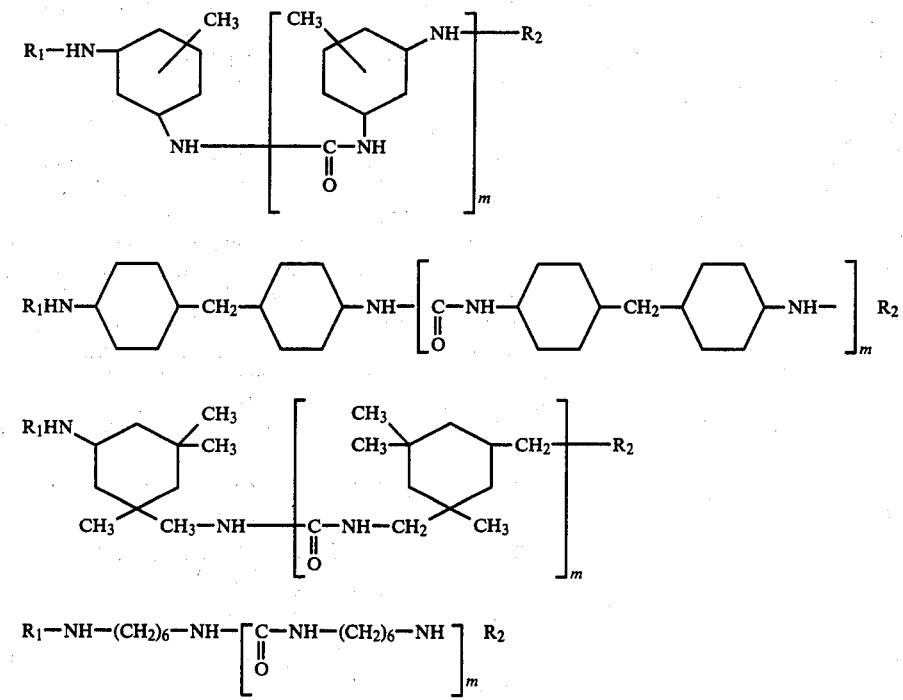

wherein
m represents an integer or, in the case of statistical mixtures, a fractional number of from 1 to 10; and
$R_1$ and $R_2$ which may be the same or different, represent —H, —COOR$_3$, —CONH$_2$, —CONHR$_3$, wherein $R_3$ represents a monovalent organic radical and preferably a $C_1$-$C_4$ alkyl radical.

The corresponding diureas or the N,N'-disubstituted simple ureas exemplified are preferably used.

Suitable ureas also include, for example, the N,N'-disubstituted ureas or the corresponding polyureas which are produced as by-products in the processes described in U.S. Pat. Nos. 2,409,712 and 2,806,051. However, correspondingly substituted ureas (D. F. Kutepow, Russ. Chem. Rev. 31, 633 (1962)) or polyureas (H. Rinke, Houben-Weyl XIV/2, 165 ff) may also be synthesized by other methods.

Particularly suitable N,N'-disubstituted linear polyureas are also easily obtained by the reaction of the diamine component with aliphatic carbonic esters of the type mentioned below, N,N'-disubstituted ureas or polyureas having terminal urethane groups of the type mentioned above in the definition of $R_1$ and $R_2$ being formed when an excess of carbonic acid is used.

Reactants for the substituted ureas include aliphatic carbonic esters, such as dimethyl-, diethyl-, dipropyl-, diisopropyl-, dibutyl-, dicyclohexyl-, diisooctyl-, and didodecylcarbonate, mixed carbonic esters, such as methylisopropyl- and ethylphenyl- carbonate, cyclic carbonic esters having at least six ring members, such as trimethylene carbonate, 2,2-dimethyl trimethylene carbonate, bishexamethylene-dicarbonate and linear polycarbonates, such as tetramethylene- and hexamethylene- polycarbonate. Dialkyl carbonates having unsubstituted $C_1$–$C_4$ alkyl radicals are preferred. The di- and poly-carbonates are generally used as reactants for monoureas. The dialkyl carbonates may be obtained, for example, as described in German Offenlegungsschrift No. 2,748,718, from carbon dioxide and alcohols using ethylene oxide as a dehydration agent.

The process according to the present invention is preferably conducted in the presence of suitable catalysts. These include inorganic or organic compounds of aluminum, lead, magnesium, titanium, zinc, tin or zirconium. It is particularly preferred to use organic compounds of the above-mentioned metals which are at least partially soluble in the reaction mixture, although lead dioxide is also a preferred catalyst. Suitable catalysts include, for example, the oxides or hydroxides, salts or alcoholates of the above-mentioned metals, as well as organometallic compounds of the above-mentioned metals wherein the organic radical is bonded to the metal in a homopolar manner. Suitable catalysts include zinc oxide; zinc acetate; zinc stearate; zinc naphthenate; the corresponding magnesium compounds; aluminum triethylate and -triisopropylate; dibutyl tin oxide; dibutyl tin chloride; dibutyl tin dilaurate; diacetates, chlorides or laurates of divalent or tetravalent tin; dioxides, acetates or naphthenates of divalent lead; titanium tetrabutylate, -tetraisobutylate, -tetraisooctylate or -tetradodecylate; zirconium tetraethylate, -tetrapropylate, -tetraisopropylate or -tetraisooctylate; and the like.

When used, the catalysts are used in quantities of from 0.001 to 10%, preferably from 0.01 to 3%, based on the total weight of the reaction mixture.

The reaction temperatures are generally from 80° to 250° C., and preferably from 100° to 200° C. The process may be carried out under normal or elevated pressure. An elevated pressure is always necessary if low-boiling carbonates are to be reacted in the medium or higher temperature range.

When conducting the process according to the present invention, at least 1 mol of aliphatic carbonic ester is generally used per gram equivalent of urea groups. The reactants are generally used in a stoichiometric ratio, as a smooth reaction then leads to the product without by-products according to the reaction equation. However, it may be advantageous in many cases to use an excess of carbonic esters, as they may act as solvents for sparingly melting or sparingly soluble starting materials, for example aromatic ureas or polyureas.

Upon completion of the reaction according to the present invention, the reaction mixtures may be worked-up by distillation or by recrystallization in a known manner and by filtration of any insoluble by-products or unreacted starting material. The N,O-disubstituted urethanes formed during the process according to the present invention correspond, with respect to the N-substituents thereof, to the N-substituents of the ureas used and, with respect to the O-substituents thereof, to the hydrocarbon radicals of the carbonic esters used. The urethanes obtainable according to the present invention may be split by the action of heat in a known manner into the isocyanate component thereof and the alcohol component thereof.

The percentages given in the following Examples are percentages, by weight.

EXAMPLES 1 TO 9

N,N'-diphenylurea, diethylcarbonate and catalyst are heated in a small pressure vessel. After cooling, the vessel is opened, the contents filtered to separate unreacted urea and the filtrate analyzed by gas chromatography. The conversion of diphenylurea and the conversion yield of N-phenyl-O-ethylurethane are determined in this way. The following Table shows the molar ratios, reaction conditions and experimental results.

DEC=Diethylcarbonate
DPH=Diphenylurea
PU=N-phenyl-O-ethylurethane

| No | Mol. ratio DEC/DPH | %, by wt. catalyst rel. reaction mixture | | Temp. °C. | Time hrs. | Conversion of DPH | % of theoretical yield of PU rel. conversion of DPH |
|---|---|---|---|---|---|---|---|
| 1 | 6/1 | $Mg(OCOC_{17}H_{35})_2$ | 0.8 | 180 | 6 | 100 | 97 |
| 2 | 6/1 | $Zn(OCOC_{17}H_{35})_2$ | 0.8 | 180 | 6 | 100 | 98 |
| 3 | 6/1 | Pb O | 0.8 | 180 | 3 | 100 | 98 |
| 4 | 6/1 | $Pb(OCOCH_3)_2$ | 0.8 | 180 | 3 | 100 | 98 |
| 5 | 6/1 | $Sn(OCOC_{11}H_{23})_2$ | 1.6 | 180 | 6 | 100 | 92 |
| 6 | 6/1 | $(C_4H_9)_2SnO$ | 0.8 | 180 | 6 | 75 | 90 |
| 7 | 9/1 | $(C_4H_9)_2SnO$ | 0.2 | 200 | 5 | 90 | 92 |
| 8 | 6/1 | $Ti(OC_4H_9)_4$ | 0.8 | 180 | 2 | 100 | 99 |
| 9 | 6/1 | Octasoligen Zircon | 0.8 | 180 | 6 | 100 | 93 |

EXAMPLE 10

35.4 g (1/6 mol) of N,N'-diphenylurea, 118 g (1 mol) of diethyl carbonate and 1.7 g of titanium tetrabutylate are refluxed for 7 hours, the internal temperature being from 127° to 131° C. A fraction which boils at from 93° to 98° C./2 mb (the N-phenyl-O-ethylurethane) is obtained in addition to the excess diethylcarbonate by fractional distillation of the reaction mixture. Yield 53.5 g=97.5% of the theoretical yield.

EXAMPLE 11

42.4 g (0.2 mol) N,N'-diphenylurea, 35 g (0.2 mol) of dibutylcarbonate and 2 g zirconium tetrapropylate are heated to 190° C. for 3½ hours. The diphenylurea dissolved after 1 hour. The reaction product is precipitated in crystalline form after cooling. 68 g of N-phenyl-O-butylurethane corresponding to 88% of the theoretical yield are obtained after recrystallization from 250 ml ligroin.

Melting point=60°/61° C.

EXAMPLE 12

37 g of a polyurea (obtained from 0.25 mol of 2,4-diaminotoluene and 1.5 mol of diethylcarbonate), 177 g (1.5 mol) of diethylcarbonate and 2 g of titanium tetrabutylate are refluxed for 23 hours (internal temperature from 128° to 130° C.). The reaction mixture is diluted with methylene chloride and filtered. 24.4 g of polyurea remain as filter residue. 22 g of m-toluylene-bisethyl-urethane having a melting point of 134°-136° C. are obtained from the filtrate. Yield is 97% based on 33% conversion. A comparison sample produced from 2,4-diaminotoluene and chlorocarbonic acid ethylester proved to be identical.

EXAMPLE 13

23 g of polyurea (obtained from 0.1 mol of 4,4'-diaminodiphenylmethane and 0.6 mol of diethylcarbonate), 34.8 g of di-n-butylcarbonate and 2 g of titanium tetrabutylate are maintained at from 192° to 205° C. for 14 hours. The reaction product is boiled with methylene chloride and the unreacted polyurea (16 g) filtered off. The filtrate is concentrated and distilled. Unreacted dibutyl carbonate passes over at 92° C./18 Torr, the residue is recrystallized from toluene/ligroin 6.8 g of 4,4'-bis-(n-butoxycarbonyl amino)-diphenyl methane having a elting point of from 112°-113.5° C. is obtained. Yield 95% based on the conversion.

EXAMPLE 14

17.2 g (0.1 mol) of N,N'-dibutylurea, 35.4 g (0.3 mol) of diethylcarbonate and 1 g of titanium tetrabutylate are refluxed for 25 hours. The excess diethyl carbonate is distilled off and the N-butylethyl urethane ($n^{20}$=1.4298) is allowed to pass over at from 89°—$D$91°/7 Torr. Dibutylurea (12.1 g) remains as residue. Yield: 7.2 g=99%, based on the reacted dibutylurea.

EXAMPLE 15

42.4 g (0.2 mol) of N,N'-diphenylurea, 26 g (0.2 mol) of neopentylglycol carbonate and 2 g of titanium tetrabutylate are heated to 200° C. for 5 hours. The reaction product is dissolved in 500 ml hot toluene, filtered from the undissolved diphenylurea (9.1 g) and allowed to crystallize out. 35 g of bisphenylurethane of neopentylglycol having a melting point of from 136°-138° C. are obtained. Yield 64%, based on the conversion.

EXAMPLE 16

42.2 g (0.2 mol) of N,N'-diphenylurea, 28.8 g of hexamethylene polycarbonate (OH-number 39) and 2 g of titanium tetrabutylate are heated to 200° C. for 1½ hours. The reaction product is recrystallized from toluene. 3.8 g of diphenylurea remain undissolved. 42 g of bisphenyl urethane of hexane diol having a melting point of from 165°-166° C. are obtained. Yield 60% based on the conversion.

EXAMPLE 17

26 g of N,N'-diphenylurea, 26 g of dibutyl carbonate and 1 g of aluminum isopropylate are heated to 190° C. for 2½ hours. The reaction product is dissolved in methylene chloride and the unreacted diphenylurea (3.5 g) filtered off. The solution is stirred for 1 hour with 20 g of acid—activated Fuller's earth and suction filtered. 27 g of N-phenylbutyl urethane are obtained by distillation at from 100°-105° C./0.03 Torr. Melting point 60°-61° C. Yield 57% of the theoretical yield=66% based on the conversion.

EXAMPLE 18

42.4 g (0.2 mol) of N,N'-diphenylurea, 118 g (1 mol) of diethyl carbonate and 1.7 g of lead oxide are refluxed for 7 hours. The process is carried out as in Example 8. 55 g of N-phenylethyl urethane are obtained at from 80° to 85° C./0.06 Torr. Melting point 47°-48° C., yield 83% of the theoretical yield.

EXAMPLE 19

Example 9 is repeated using 1.7 g of zinc stearate as catalyst. Reaction time 22 hours. 15 g of diphenylurea unreacted. Yield of N-phenylethyl urethane: 37 g=56% of the theoretical yield=87% based on the conversion.

What is claimed is:

1. A process for the production of N,O-disubstituted urethanes comprising reacting N-mono or N,N'-disubstituted ureas or linear polyureas with aliphatic carbonic esters in the presence of inorganic or organic compounds of aluminum, lead, magnesium, titanium, tin, zinc or zirconium as catalyst.

2. The process of claim 1, characterized in that organic compounds of aluminum, lead, magnesium, titanium, zinc, tin or zirconium which are at least partially soluble in the reaction mixture are used as catalysts.

3. The process of claim 1 characterized in that lead oxide is used as catalyst.

4. The process of claim 1, wherein the catalyst is used in an amount of from 0.001 to 10% by weight based on the total weight of the reaction mixture.

5. The process of claim 1 wherein the reaction temperature is from 80° to 250° C.

6. The process of claim 1 wherein at least one mol of aliphatic carbonic ester is used per gram equivalent of urea groups present.

* * * * *